United States Patent
Marhold et al.

(10) Patent No.: US 6,706,918 B2
(45) Date of Patent: Mar. 16, 2004

(54) 3-CYANO-2,4,5-TRIFLUORO-BENZOYL FLUORIDE AND INTERMEDIATE PRODUCTS FOR THE PRODUCTION THEREOF

(75) Inventors: Albrecht Marhold, Leverkusen (DE); Peter Wolfrum, Monheim (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/277,310

(22) Filed: Oct. 22, 2002

(65) Prior Publication Data

US 2003/0092929 A1 May 15, 2003

Related U.S. Application Data

(60) Continuation of application No. 09/814,132, filed on Mar. 21, 2001, now Pat. No. 6,541,675, which is a division of application No. 09/403,263, filed on Oct. 15, 1999, now Pat. No. 6,229,040.
(60) Provisional application No. PCT/EP98/02175, filed on Apr. 14, 1998.

(30) Foreign Application Priority Data

Apr. 24, 1997 (DE) .......................... 197 17 231

(51) Int. Cl.$^7$ .............................. C07C 65/30
(52) U.S. Cl. ..................................... 562/459
(58) Field of Search ............................. 562/458

(56) References Cited

U.S. PATENT DOCUMENTS 6,323,213 B1 * 11/2001 Bartel et al. ............... 514/300

FOREIGN PATENT DOCUMENTS

| DE | 3615767 | 12/1987 |
| DE | 3702393 | 11/1998 |
| EP | 0307897 | 3/1989 |
| WO | 9731001 | 8/1997 |

* cited by examiner

*Primary Examiner*—Alan L. Rotman
*Assistant Examiner*—Ebenezer Sackey
(74) *Attorney, Agent, or Firm*—Susan M. Pellegrino

(57) ABSTRACT

The present invention relates to 3-cyano-2,4,5-trifluorobenzoyl fluoride and to intermediates for its preparation and to the process for the preparation of 3-cyano-2,4,5-trifluoro-benzoyl fluoride, which starts from 5-fluoro-1,3-xylene (VIII); which is bichlorinated in the ring in the presence of a catalyst under ionic conditions to give 2,4-dichloro-5-fluoro-1,3-dimethylbenzene (VII). The latter is chlorinated in the side chains under free-radical conditions to give 2,4-dichloro-5-fluoro-3-dichloromethyl-1-trichloromethylbenzene (VI). The latter is hydrolyzed via 2,4-dichloro-5-fluoro-3-dichloromethylbenzoic acid (V), which can be isolated if necessary, to give 2,4-dichloro-5-fluoro-3-formyl-benzoic acid (IV), the aldehyde group of which is reacted to give 2,4-dichloro-5-fluoro-3-N-hydroxyiminomethyl-benzoic acid (III), from which, with simultaneous conversion of the carboxyl group into the chlorocarbonyl group, water is eliminated using an acid chloride to give the nitrile 2,4-dichloro-3-cyano-5-fluoro-benzoyl chloride (II). Finally, the nitrile is subjected to fluorine/chlorine exchange.

2 Claims, No Drawings

3-CYANO-2,4,5-TRIFLUORO-BENZOYL FLUORIDE AND INTERMEDIATE PRODUCTS FOR THE PRODUCTION THEREOF

This application is a continuing application of U.S. Ser. No. 09/814,132, filed Mar. 21, 2001 now U.S. Pat. No. 6,541,675, which is a divisional application of U.S. Ser. No. 09/403,263, filed Oct. 15, 1999 which issued as U.S. Pat. No. 6,229,040 which is a 371 of PCT/EP98/02175, filed Apr. 14, 1998.

The present invention relates to 3-cyano-2,4,5-trifluoro-benzoyl fluoride, to a process for its preparation, and to other novel halogenobenzene derivatives as intermediates.

3-Cyano-2,4,5-trifluoro-benzoyl chloride can be used for the preparation of antiinfective quinolonecarboxylic acids (cf. DE-A 1 963 805 No.19 606 762.6=WO 97/31001). The preparation starts from 2,4-dichloro-5-fluoro-3-cyanobenzoic acid and leads by a known method (cf. DE 3702393 A1) to 2,4-dichloro-3-cyano-5-fluoro-benzoyl chloride, which is then fluorinated. A disadvantage of this process is, in particular, the Sandmeyer reaction, which proceeds with poorly reproducible yield, using a molar amount of copper cyanide and an additional three-fold excess of sodium cyanide to give 2,4-dichloro-3-cyano-5-fluoro-benzoic acid. The use of such large amounts of cyanide also harbours a considerable hazard potential when the reaction is carried out industrially.

The present invention relates to novel 3-cyano-2,4,5-trifluoro-benzoyl fluoride of the formula (I)

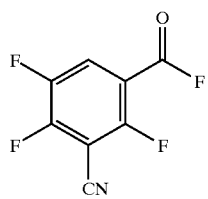

(I)

The invention also relates to a process for the preparation of 3-cyano-2,4,5-trifluoro-benzoyl chloride by chlorination of 3-cyano-2,4,5-trifluoro-benzoyl fluoride.

In addition, the invention also relates to the use of 3-cyano-2,4,5-trifluoro-benzoyl fluoride for the synthesis of quinolones.

The invention further relates to a multistage process for the preparation of 3-cyano-2,4,5-trifluoro-benzoyl fluoride, which starts from 5-fluoro-1,3-xylene (VIII), characterized in that 5-fluoro-1,3-xylene (VIII) is bichlorinated in the ring in the presence of a catalyst under ionic conditions to give 2,4-dichloro-5-fluoro-1,3-dimethylbenzene (VII), which is then chlorinated in the side chains under free-radical conditions to give 2,4-dichloro-5-fluoro-3-dichloromethyl-1-trichloromethylbenzene (VI), which is hydrolysed via 2,4-dichloro-5-fluoro-3-dichloromethylbenzoic acid (V), which can be isolated if necessary, to give 2,4-dichloro-5-fluoro-3-formyl-benzoic acid (IV), the aldehyde group of which is reacted to give 2,4-dichloro-5-fluoro-3-N-hydroxyiminomethyl-benzoic acid (III), from which, with simultaneous conversion of the carboxyl group into the chlorocarbonyl group, water is eliminated using an acid chloride to give the nitrile 2,4-dichloro-3-cyano-5-fluoro-benzoyl chloride (II), which, finally, is subjected to fluorine/chlorine exchange.

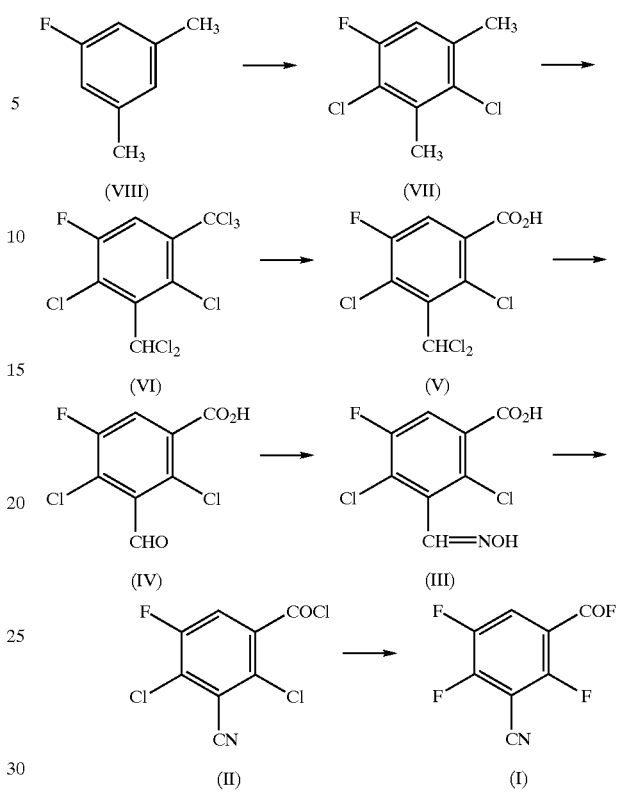

Alternatively, 2,4-dichloro-5-fluoro-3-formyl-benzoic acid (IV) can also be reacted to give 2,4-dichloro-5-fluoro-3-cyano-benzoic acid (IX), which can then be converted into the acid chloride (II).

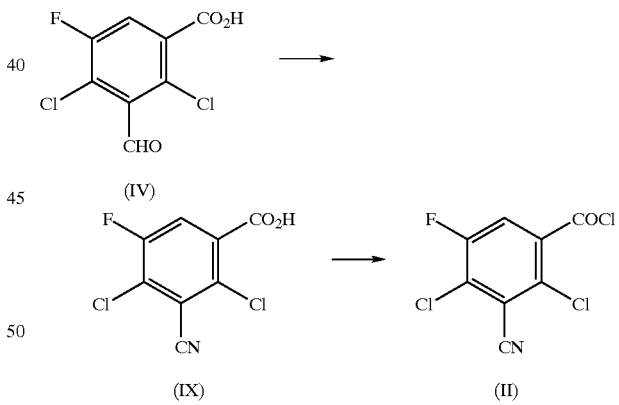

The intermediates of the formulae (III) to (VII) are novel without exception and are likewise provided by the invention.

3-Cyano-2,4,5-trifluoro-benzoyl fluoride is an intermediate, readily obtainable by the process described here, for the preparation of 3-cyano-2,4,5-trifluoro-benzoyl chloride.

The process according to the invention is described in more detail below.

The ring chlorination of commercially available 5-fluoro-1,3-xylene (VIII) to give 2,4-dichloro-5-fluoro-1,3-dimethylbenzene (VII) is carried out using chlorine gas.

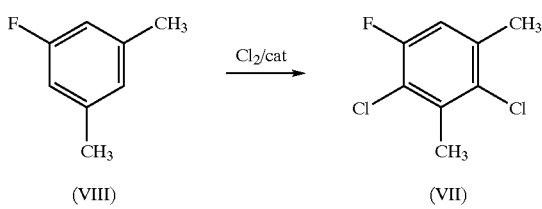

2,4-Dichloro-5-fluoro-1,3-dimethylbenzene (VII) is novel.

The catalyst used is one or more Friedel-Crafts catalysts, preferably a Lewis acid, such as, for example, iron (III) chloride or aluminium chloride. For example, from 0.1 to 10 mol %, preferably from 0.2 to 2 mol %, based on 5-fluoro-1,3-xylene, are used.

The reaction can be carried out at temperatures below room temperature or at slightly elevated temperature. Preference is given to temperatures between 0 and 40° C.

The chlorination can be carried out without a diluent or in a suitable inert diluent. Particularly suitable diluents are halogenated hydrocarbons such as dichloro-, trichloro-, tetrachloromethane, 1,2-dichloroethane or 1,2,4-trichlorobenzene. The chlorination can be carried out continuously or batchwise. In a continuous process, it is wise to proceed only to a low conversion because the chlorination does not take place with complete selectivity. In the batchwise procedure, chlorine is introduced in an amount up to approximately 0.8–1.1 times, preferably 0.8–0.95 times, the theoretical amount, the reaction mixture achieving a solid consistency in the chlorination without diluent. It is also advantageous in this connection to proceed only up to this not-too-high conversion because then the losses as a result of superchlorination on the one hand and the space-time yield on the other are in an optimum range.

The mixture is worked up, for example, by fractional distillation. It is advantageous to return recovered starting material and monochlorinated compounds to the process.

The side-chain chlorination of 2,4-dichloro-5-fluoro-1,3-dimethylbenzene (VII) to give 2,4-dichloro-5-fluoro-3-dichloromethyl-1-trichloromethylbenzene (VI) is preferably carried out without a diluent using chlorine gas.

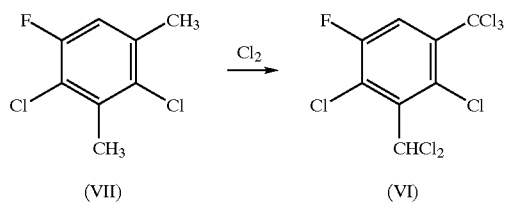

2,4-Dichloro-5-fluoro-3-dichloromethyl-1-trichloromethylbenzene (VI) is novel.

The conditions for the free-radical reaction are achieved by elevated temperature and optional irradiation with a light source or addition of a customary free-radical initiator. Suitable light sources are incandescent lamps such as, preferably, halogen lamps or medium- or high-pressure mercury vapour lamps. Suitable free-radical initiators are, for example, benzoyl peroxide, di-tert-butyl peroxide or 2,2-azobis(isobutteronitrile) (AIBN). The reaction temperature can be between 80 and 200° C., preferably 100 and 180° C., particularly preferably between 120 and 170° C.

The chlorination can be carried out continuously or batchwise. In a continuous process, it is wise to proceed only up to a low conversion because the chlorination does not take place with complete selectivity. In the batchwise procedure, chlorine is introduced in an amount up to approximately 0.8–1.2 times, preferably 0.95–1.15 times the theoretical amount, corresponding to from 40 to 75%, preferably from 65 to 75%, conversion to the desired product.

The reaction mixture can be worked up, for example, by fractional distillation or recrystallization from a suitable solvent such as, for example, methanol. Preference is given to distillation. Insufficiently chlorinated compounds can be introduced again into the chlorination.

The chlorinated side chains are hydrolysed using a protic acid, optionally in the presence of water. Suitable protic acids are mineral acids such as, for example, sulphuric acid, hydrochloric acid or phosphoric acid, and organic acids such as, for example, formic acid, acetic acid or oxalic acid, and mixtures thereof and with a protic solvent such as, for example, water.

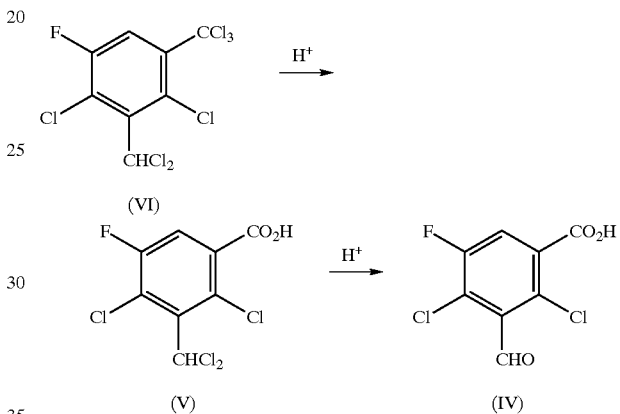

Depending on the type, concentration and amount of acid and reaction temperature, it is possible to carry out the hydrolysis of 2,4-dichloro-5-fluoro-3-dichloromethyl-1-trichloromethylbenzene (VI) to give 2,4-dichloro-5-fluoro-3-formyl-benzoic acid (IV) in one or two steps. Because the trichloromethyl group is hydrolysed significantly more quickly, 2,4-dichloro-5-fluoro-3-dichloromethylbenzoic acid (V) can, if the reaction conditions are suitable, be isolated directly and converted to (IV) in a further hydrolysis step. As far as the overall process of the preparation of 3-cyano-2,4,5-trifluoro-benzoyl fluoride according to the invention is concerned, it is advantageous to carry out the hydrolysis in one step.

2,4-Dichloro-5-fluoro-3-formyl-benzoic acid (IV) and 2,4-dichloro-5-fluoro-3-dichloromethylbenzoic acid (V) are novel.

The amount of protic acid is unimportant. The acid, for example, is initially introduced and the molten aromatic compound (VI) or (V) is added. Preference is given to using sufficient acid (mixture) for the reaction mixture to remain stirrable.

The temperature for the hydrolysis can be varied within a wide range depending on the desired product, acid and reaction time. The temperature is generally from 0 to 100° C.

The product can be isolated, for example, by precipitation with water and removal by filtration or extraction.

The oxime (III) is prepared from 2,4-dichloro-5-fluoro-3-formyl-benzoic acid (IV) by a generally known method.

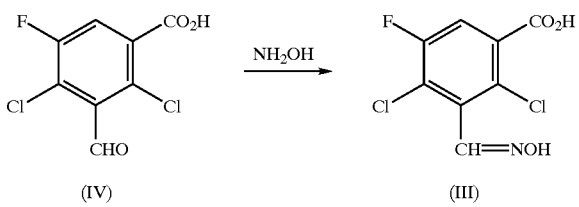

(IV)     (III)

2,4-Dichloro-5-fluoro-3-N-hydroxyiminomethyl-benzoic acid (III) is novel.

The reagent used is a salt of hydroxylamine such as, for example, the hydrochloride or sulphate, or also the free base.

If a salt of hydroxylamine is used, the reaction is carried out in the presence of an acid acceptor. Suitable acid acceptors are customary inorganic or organic bases. These include, preferably, the hydroxides, alkoxides, acetates, carbonates and hydrogen carbonates of alkaline earth metals or alkali metals, such as, for example, the hydroxides of sodium, potassium or ammonium, sodium methoxide, sodium ethoxide, potassium tert-butoxide, the acetates of sodium, potassium, calcium or ammonium, the carbonate of sodium, potassium or ammonium, the hydrogen carbonates of sodium or potassium, and tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The reaction is carried out in the presence of a diluent. Suitable diluents are water, organic solvents and any mixtures thereof. Examples which may he mentioned are ethers, such as diethyl ether, diisopropyl ether, methyl t-butyl ether, methyl t-amyl ether, dioxane, tetrahydrofuran, 1,2-dimethoxyethane, 1,2-diethoxyethane, diethylene glycol dimethyl ether or anisole; nitriles, such as acetonitrile, propionitrile, n- or i-butyronitrile; alcohols, such as methanol, ethanol, n- or i-propanol, n-, iso-, sec- or tert-butanol, ethanediol, propane-1,2-diol, ethoxyethanol, methoxyethanol, diethylene glycol monomethyl ether, diethylene glycol monoethyl ether; water.

The temperature for the reaction can be varied within a relatively wide range. It is generally chosen to be between 10 and 100° C., preferably between 20 and 80° C.

Per mol of formylbenzoic acid (IV), from 1 to 1.5 equivalents of hydroxylamine (salt) are used, and from 200 to 2000 ml, preferably from 500 to 1000 ml, of diluent are used. Per equivalent of hydroxylamine, from 1 to 5, preferably from 1.1 to 3, equivalents of acid acceptor are used.

For work-up, the reaction mixture is acidified, for example using a mineral acid, and, where appropriate, the product is extracted using a suitable solvent such as, for example, methyl tert-butyl ether, or the solid is filtered off.

If the reaction of (IV) with hydroxylamine or a salt of hydroxylamine is carried out in the presence of formic acid, then the reaction product obtained is the nitrile (IX). Preference is given to using hydroxylamine hydrochloride.

The reaction can be carried out in the presence of a diluent. Suitable diluents are water, organic solvents and any mixtures thereof. Preferably, the reaction is carried out in from 85% to 98% strength aqueous formic acid.

The temperature of the reaction can be varied in a relatively wide range. It is generally chosen to be between 10 and 120° C., preferably between 50 and 110° C.

Per mol of (IV), from 1 to 1.5 equivalents of hydroxylamine (salt) are used, and from 100 to 3000 ml, preferably from 500 to 1500 ml, of aqueous formic acid are used.

The starting materials can be added in different orders. For example, all of the starting materials can be initially introduced and then heated up to the reaction temperature together. It is, however, also possible to initially introduce the hydroxylamine (salt) into the aqueous formic acid, and introduce the starting material (IV) at the reaction temperature.

Alternatively, the starting material (IV), which can also be used moistened with sulphuric acid, can be introduced into the aqueous formic acid, and the hydroxylamine (salt) or a solution of the hydroxylamine (salt) in water or aqueous formic acid can be metered in at the reaction temperature.

For work-up, the mixture is further diluted with water, and (IX) is filtered off as solid.

3-Cyano-2,4-dichloro-5-fluorobenzoic acid (IX) is converted into benzoyl chloride (II) using a chlorinating agent as reagent.

Suitable chlorinating agents are those agents given below under the reaction conditions stated there.

The preparation of 2,4-dichloro-3-cyano-5-fluoro-benzoyl chloride (II) by elimination of water from 2,4-dichloro-5-fluoro-3-N-hydroxyiminomethyl-benzoic acid (III) with simultaneous conversion of the carboxylic acid function into the carbonyl chloride takes place using a chlorinating agent as reagent.

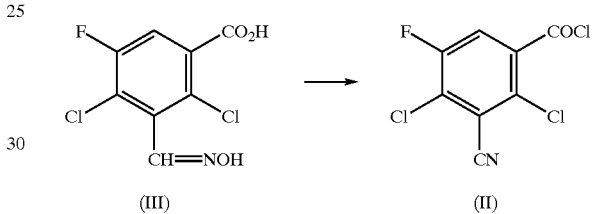

(III)     (II)

Suitable chlorinating agents are inorganic or organic acid chlorides, such as, for example, phosgene (carbonyl dichloride) or the synthetic equivalents trichloromethyl chloroformate or bis(trichloromethyl) carbonate, oxalyl chloride, acetyl chloride, thionyl chloride, sulphuryl chloride, phosphorous trichloride, phosphorous pentachloride or phosphorous oxychloride and mixtures thereof. Preference is given to phosgene or thionyl chloride.

The reaction can be carried out in the presence or absence of a suitable diluent. Suitable diluents for this purpose are organic solvents, an acid chloride which is liquid under the reaction conditions, i.e. the reagent itself, and any mixtures thereof. Examples of organic solvents which may be mentioned are: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, tetrachloromethane, dichloroethane, trichloroethane or tetrachloroethylene; ethers, such as diethyl ether, diisopropyl ether, methyl t-butyl ether, methyl t-amyl ether, dioxane, tetrahydrofuran, 1,2-dimethoxyethane, 1,2-diethoxyethane, diethylene glycol dimethyl ether or anisole.

The oxime compound and chlorinating agent can be added in any order. In a preferred embodiment, the solvent-free reagent is initially introduced, and 2,4-dichloro-5-fluoro-3-N-hydroxyiminomethyl-benzoic acid is metered in continuously or in portions at a rate of controllable gas evolution (hydrogen chloride and in some cases other gases such as carbon dioxide or sulphur dioxide).

From 2 to 10 mol of acid chloride are generally used per mol of compound (III). It is also possible to use a larger excess, particularly when the acid chloride also serves as diluent.

The temperature in the reaction can be varied in a relatively wide range. It is generally chosen to be between 0 and 150° C., preferably between 30° C. and boiling temperature. The process is generally carried out under atmospheric pressure. It is also possible to carry out the reaction under reduced or elevated pressure. For example, when phosgene is used, it is wise to keep it liquid at a temperature above the boiling point at atmospheric pressure and to release the gases which are liberated by means of a pressure-relief device.

The mixture can be worked up, for example, by fractional distillation.

The final fluorine/chlorine exchange takes place nucleophilically using a fluoride source.

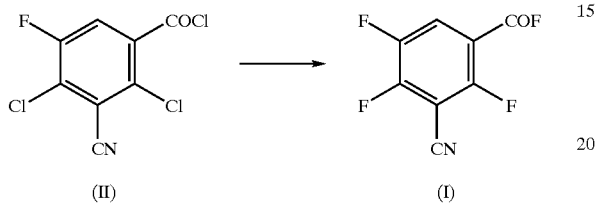

(II)     (I)

Suitable fluoride sources are, for example, metal fluorides, preferably alkali metal fluorides, such as, for example, potassium fluoride or caesiuim fluoride.

The fluorination is carried out in the presence of a diluent. Suitable diluents are polar aprotic solvents such as, for example, amides, such as N,N-dimethylformamide, N,N-dimethylacetamide, N-methylformanilide, N-methylpyrrolidone or hexamethyl-phosphoramide; ureas, such as N,N-dimethylpropyleneurea, N,N-dimethylethyleneurea; sulphoxides, such as dimethyl sulphoxide; sulphones, such as sulpholane.

The fluorination can also be carried out in the presence of known catalysts for halex reactions.

Per mol of 2,4-dichloro-3-cyano-5-fluoro-benzoyl chloride, from 3 to 10 mol, preferably from 3.4 to 8 mol, particularly preferably from 3.7 to 6 mol of fluoride are used.

The fluorination is carried out at elevated temperature. The temperature is generally from 100 to 250° C., preferably from 130 to 200° C.

Work-up can, for example, involve distillation of the product under reduced pressure, or extraction using a solvent and subsequent fractional distillation.

The preparation of 3-cyano-2,4,5-trifluoro-benzoyl chloride from 3-cyano-2,4,5-trifluoro-benzoyl fluoride (I) according to the invention is carried out analogously to known processes for the rechlorination of carbonyl fluorides. Reagents which are suitable for this purpose are silicon chlorides, such as, for example, silicon tetrachloride, trimethylchlorosilane or dimethyldichlorosilane; or calcium chloride, in each case in the presence of catalytic amounts of a Lewis acid, such as, for example, aluminium chloride or boron trichloride; or said or other chlorine-containing Lewis acids themselves.

Per mol of compound (I), from 1 to 2 equivalents of reagent and, where appropriate, from 0.01 to 0.1 mol of Lewis acid are generally used.

The temperature in the reaction can be varied within a relatively wide range. The reaction is generally carried out at from 20 to 150° C. when silicon chlorides and Lewis acids are used, and at from 120 to 200° C. when calcium chloride is used.

Work-up is preferably by vacuum distillation.

It is extremely surprising that the ring chlorination of 5-fluoro-1,3-xylene to give 2,4-dichloro-5-fluoro-1,3-dimethylbenzene proceeds with very high selectivity, without which the synthesis sequence according to the invention would not be possible.

Further details of the processes are given in the examples below, without the invention being limited thereby.

EXAMPLE 1

Preparation of 2,4-dichloro-5-fluoro-1,3-dimethylbenzene

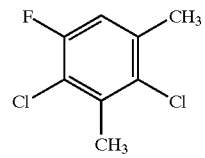

a) Solvent-Free 1 g of anhydrous iron(III) chloride were introduced into 124 g of 3,5-dimethyl-fluorobenzene, and chlorine was introduced at the rate of the reaction (about 4 h). The reaction is initially slightly exothermic (temperature increase from 24 to 32° C.) and was maintained below 30° C. by gentle cooling. After 120 g of chlorine had been introduced, the mixture solidified. According to GC analysis, 33.4% of monochlorinated compound, 58.4% of desired product and 5% of superchlorinated compounds had formed. After the hydrogen chloride had been stripped off, distillation was carried out in a water-jet vacuum on a column.

In the initial fraction, at 72–74° C./22 mbar, 49 g of 2-chloro-5-fluoro-1,3-dimethylbenzene were obtained. After an intermediate fraction of 5 g, at 105° C./22 mbar, 75 g of 2,4-dichloro-5-fluoro-1,3-dimethylbenzene passed over.

Melting range: 64–65° C.

b) In 1,2-dichloroethane 1 kg of 3,5-dimethyl-fluorobenzene and 15 g of anhydrous iron(III) chloride were introduced into 1 l of 1,2-dichloroethane, and chlorine was introduced at the rate of the reaction (about 4 h). The reaction is initially slightly exothermic (temperature increase from 24 to 32° C.) and was maintained below 30° C. by gentle cooling. After 1200 g of chlorine had been absorbed, according to GC analysis, 4% of monochlorinated compound, 81.1% of desired product and 13.3% of superchlorinated compounds had formed. After the solvent and hydrogen chloride had been distilled off, distillation was carried out in a water-jet vacuum on a column.

In the initial fraction, 40 g of 2-chloro-5-fluoro-1,3-dimethylbenzene were obtained. After a small intermediate fraction, 1115 g of 2,4-dichloro-5-fluoro-1,3-dimethylbenzene passed over at 127–128° C./50 mbar.

EXAMPLE 2

2,4-Dichloro-5-fluoro-3-dichloromethyl-1-trichloromethylbenzene

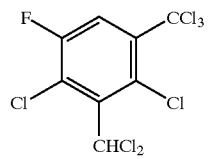

1890 g of 2,4-dichloro-5-fluoro-1,3-dimethylbenzene were introduced into a photochlorination apparatus with chlorine inlet and outlet for the hydrogen chloride to a scrubber and a light source in the vicinity of the chlorine inlet pipe, and chlorine was metered in at from 140 to 150° C. After 30 h, 3850 g of chlorine had been introduced. The content of desired product was 71.1% according to GC analysis; the proportion of insufficiently chlorinated compounds was 27.7%.

Distillation over a 60 cm column containing Wilson spiral gave an initial fraction of 1142 g, which could be reintroduced into the chlorination. The main fraction at 160–168° C./0.2 mbar gave 2200 g of 2,4-dichloro-5-fluoro-3-dichloromethyl-1-trichloromethylbenzene having a melting range of 74–76° C.

After recrystallization of a sample from methanol, tile melting point was 81–82° C. The initial fraction from this reaction can be reintroduced into the chlorination with new starting material (1555 g). This gave 1377 g of initial fraction and 2465 g of main fraction with a purity of 97.4%.

EXAMPLE 3

2,4-Dichloro-5-fluoro-3-formyl-benzoic acid

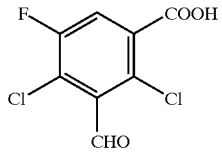

At 70° C., 2500 ml of 95% strength sulphuric acid were initially introduced into a stirred apparatus fitted with a gas outlet, and 500 g of molten 2,4-dichloro-5-fluoro-3-dichloromethyl-1-trichloromethylbenzene were added dropwise with stirring. After a short while, evolution of hydrogen chloride commenced. After 2 h everything had been metered in and stirring was continued until the evolution of gas ceased. After the reaction mixture had cooled to 20° C., it was discharged onto 4 kg of ice, and the precipitated solid was filtered off with suction. The product was then washed with water and dried. The yield of 2,4-dichloro-5-fluoro-3-formyl-benzoic acid was 310 g.

Melting range: 172–174° C.

Repetition of the experiment using 2390 g of starting material, 7170 ml of sulphuric acid gave 1540 g of product (97.8% purity).

EXAMPLE 4

2,4-Dichloro-5-fluoro-3-N-hydroxyiminomethyl-benzoic acid

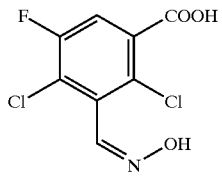

80 g of hydroxylammonium chloride in 500 ml of ethanol were introduced into a stirred apparatus, and 200 ml of 45% strength sodium hydroxide solution were added dropwise, and 200 g of 2,4-dichloro-5-fluoro-3-formyl-benzoic acid were then introduced at 40–45° C. The reaction was slightly exothermic and stirring was continued for 5 h at 60° C. After the mixture had been cooled to room temperature, the pH was adjusted to <3 by the dropwise addition of hydrochloric acid. The product was taken up in tert-butyl methyl ether, and the organic phase was separated off. The solvent was distilled off to leave 185 g of 2,4-dichloro-5-fluoro-3-N-hydroxyiminomethyl-benzoic acid.

Melting range: 190–194° C.

Repetition of this example in water instead of ethanol using 60.5 g of hydroxylammonium chloride in 363 ml of water, 150 ml of 45% NaOH, 150 g of starting material gave 150 g of product (93.4% purity).

EXAMPLE 5

2,4-Dichloro-3-cyano-5-fluoro-benzoylchloride

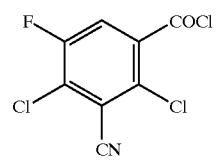

600 ml of thionyl chloride were introduced into a stirred apparatus fitted with a metering device and a gas outlet leading to a scrubber via a reflux condenser, and, at 20° C., 210 g of starting material were introduced at the rate of hydrogen chloride/sulphur dioxide evolution. At the end of the addition, the mixture was heated to reflux until the evolution of gas ceased. The mixture was then distilled. In the boiling range from 142–145° C./10 mbar, 149 g of 2,4-dichloro-3-cyano-5-fluoro-benzoylchloride were obtained (content according to GC: 98.1%).

Melting range: 73–75° C.

Repetition of this example using 450 g of phosphorous oxychloride in 200 ml of chlorobenzene as chlorinating agent gave, from 80 g of starting material (80%), 48 g of product (89.0% purity).

EXAMPLE 6

3-Cyano-2,4,5-trifluoro-benzoyl fluoride

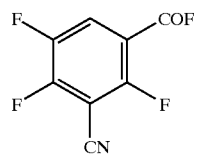

50 g of potassium fluoride were suspended in 120 ml of tetramethylene sulphone, and the suspension is dried by gently distilling it at 15 mbar (about 20 ml). 50.4 g of 2,4-dichloro-3-cyano-5-fluoro-benzoyl chloride were then added, and the mixture was stirred with the exclusion of moisture at an internal temperature of 180° C. for 12 hours. Vacuum distillation gave 32.9 g of 3-cyano-2,4,5-trifluoro-benzoyl fluoride in the boiling range from 98–100° C./12 mbar.

EXAMPLE 7

3-Cyano-2,4,5-trifluoro-benzoyl chloride

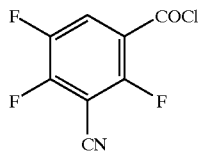

76.6 g of 3-cyano-2,4,5-trifluoro-benzoyl fluoride were initially introduced together with 1 g of anhydrous aluminium chloride at 60–65° C., and 25 g of silicon tetrachloride were then added dropwise at the rate of gas evolution. After the evolution of gas at 65° C. had ceased, the mixture was distilled under reduced pressure. In the boiling range from 120–122° C./14 mbar, 73.2 g of 3-cyano-2,4,5-trifluoro-benzoyl chloride passed over.

EXAMPLE 8

3-Cyano-2,4-dichloro-5-fluorobenzoic acid

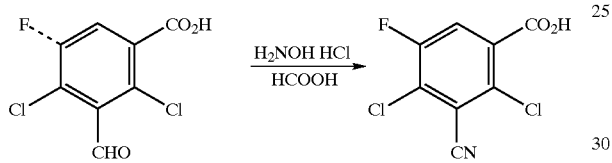

162 g of hydroxylamine hydrochloride were introduced into 2000 ml of formic acid (technical-grade, 85% strength). At 95° C., 950 g of 2,4-dichloro-5-fluoro-3-formylbenzoic acid (moistened with sulphuric acid, 42% strength) were introduced. As a result, the mixture foamed briefly and then a clear solution was immediately obtained. The mixture was then stirred for 4 hours at from 100 to 105° C. (reflux).

After the mixture had been cooled to room temperature, it was poured onto water, thoroughly stirred, filtered with suction and dried. This gave 364 g (90.3% of theory) of 3-cyano-2,4-dichloro-5-fluorobenzoic acid with a content, according to GC, of 97.7%.

EXAMPLE 9

3-Cyano-2,4-dichloro-5-fluorobenzoyl chloride 4100 ml of thionyl chloride and 41 ml of pyridine were introduced into a stirred apparatus fitted with metering device and gas outlet leading to a scrubber via a reflux condenser, and, at 20° C., 2050 g of 3-cyano-2,4-dichloro-5-fluorobenzoic acid (99.5% strength) were introduced at the rate of hydrogen chloride/sulphur dioxide evolution. At the end of the addition, the mixture was heated to reflux until the evolution of gas ceased. The mixture was then distilled. In the boiling range from 142 to 145° C./10 mbar, 2150 g (95.7% of theory) of 3-cyano-2,4-dichloro-5-fluorobenzoyl chloride were obtained (content according to GC: 98.0%).

What is claimed is:

1. 2,4-Dichloro-5-fluoro-3-formyl-benzoic acid of the formula (IV)

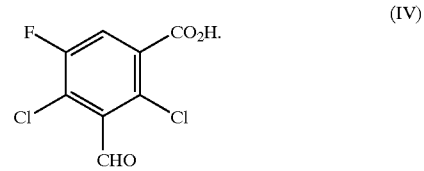

(IV)

2. Process for the preparation of 2,4-dichloro-5-fluoro-3-formyl-benzoic acid of the formula (IV) according to claim 1,

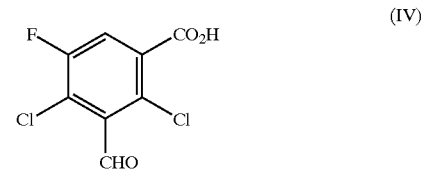

(IV)

(a) by hydrolysis of 2,4-dichloro-5-fluoro-3-dichloromethyl-benzoic acid or b) by hydrolysis of 2,4-dichloro-5-fluoro-3-dichloromethyl-1-trichloromethylbenzene of the formula (VI),

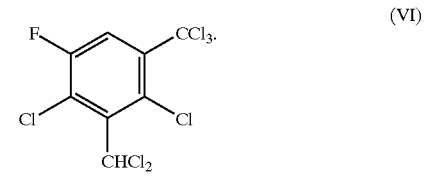

(VI)

in each case in the presence of acids and optionally in protic solvents.

* * * * *